United States Patent
Katoh et al.

(10) Patent No.: US 7,780,616 B2
(45) Date of Patent: *Aug. 24, 2010

(54) WALKING ASSISTANCE DEVICE

(75) Inventors: Hisashi Katoh, Wako (JP); Takashi Hirata, Wako (JP); Akio Koike, Wako (JP); Taiji Koyama, Wako (JP); Takako Fujii, Kyoto (JP); Yoshirou Koyama, Kyoto (JP)

(73) Assignee: Honda Motor Co., Ltd., Minato-Ku, Tokyo (JP)

( * ) Notice: Subject to any disclaimer, the term of this patent is extended or adjusted under 35 U.S.C. 154(b) by 186 days.

This patent is subject to a terminal disclaimer.

(21) Appl. No.: 10/557,338

(22) PCT Filed: Mar. 15, 2004

(86) PCT No.: PCT/JP2004/003406
§ 371 (c)(1),
(2), (4) Date: Jun. 23, 2006

(87) PCT Pub. No.: WO2004/103248
PCT Pub. Date: Dec. 2, 2004

(65) Prior Publication Data
US 2006/0258967 A1    Nov. 16, 2006

(30) Foreign Application Priority Data
May 21, 2003   (JP)  ............... 2003-143495
Sep. 4, 2003    (JP)  ............... 2003-312267

(51) Int. Cl.
*A61F 5/00* (2006.01)
*A61H 1/00* (2006.01)

(52) U.S. Cl. ............... 602/23; 602/26; 601/5; 601/33; 601/34

(58) Field of Classification Search ............... 602/23, 602/19, 26, 16; 623/27, 28, 30, 31, 39, 40, 623/43; 601/5, 33–35
See application file for complete search history.

(56) References Cited

U.S. PATENT DOCUMENTS 3,561,434 A * 2/1971 Kilbey .................. 602/36

(Continued)

FOREIGN PATENT DOCUMENTS

JP    58-163364    9/1983

(Continued)

OTHER PUBLICATIONS

Japanese Office Action, Dated Feb. 3, 2009, Issued on Japanese Patent Application No. 2003-312267.

*Primary Examiner*—Patricia M Bianco
*Assistant Examiner*—Ophelia Hawthorne
(74) *Attorney, Agent, or Firm*—Squire, Sanders & Dempsey, LLP

(57) ABSTRACT

In order to provide a walking assistance device capable of favorably providing an assisting force for maintaining the upright posture while reducing the sense of pressure when worn by the user, a hip support member (1) of the walking assisting device, which comprises an assisting force generator (hip joint actuator 10) disposed at least on a side of a hip joint to provide an assisting force to a movement of a lower limb, is provided with: a back support (4) equipped with pads (18, 19, 20) for respectively abutting an intermediate portion between right and left erector spinae muscles, lateral outer sides of the spinae muscles and right and left iliac crests; and a belt (5) connected to the back support for tightening a lower part of the rectus abdominis muscle. In this way, a supporting force can be provided to the lumbar vertebrae to steadily keep the upright posture while reducing a resistance to a bending movement of the waist caused by the support member. Further, the drive torque from the assisting force generator can be supported by the whole hip portion and this can contribute to preventing inadvertent move of the support member.

5 Claims, 7 Drawing Sheets

U.S. PATENT DOCUMENTS

| | | | |
|---|---|---|---|
| 4,622,957 A * | 11/1986 | Curlee | 602/13 |
| 4,756,306 A * | 7/1988 | Curlee | 602/19 |
| 4,905,678 A * | 3/1990 | Cumins et al. | 602/16 |
| 5,020,790 A * | 6/1991 | Beard et al. | 482/4 |
| 5,476,441 A * | 12/1995 | Durfee et al. | 602/23 |
| 5,782,782 A * | 7/1998 | Miller | 602/19 |
| 6,500,137 B1 * | 12/2002 | Molino et al. | 602/19 |
| 6,589,195 B1 * | 7/2003 | Schwenn et al. | 602/23 |

FOREIGN PATENT DOCUMENTS

| | | |
|---|---|---|
| JP | 60-199450 | 10/1985 |
| JP | 61-228854 | 10/1986 |
| JP | 63-119759 | 5/1988 |
| JP | 7-163607 | 6/1995 |
| JP | 9-253107 A | 9/1997 |
| JP | 10-248987 | 9/1998 |
| JP | 2001-214303 | 8/2001 |
| JP | 3096627 U | 9/2003 |

* cited by examiner

WALKING ASSISTANCE DEVICE

TECHNICAL FIELD

The present invention relates to a walking assistance device for providing an assisting force to the movement of the hip joint or knee joint.

BACKGROUND ART

Various proposals have been made for a walking assistance device that is adapted to mount an actuator to the hip joint or knee joint of a person having a walking impediment due to injury, disease or weakened muscle resulting from aging, so that the power from the actuator can be used to assist the movement of the lower limb.

Conventionally, it was common in such a walking assistance device to fixedly mount the actuator to the lower limb via a support member fastened on the thigh or lower leg portion by tightening a belt or the like.

The upright posture of the spine during walking is maintained by the balance of back muscle and abdominal muscle. The weakening of muscles of a person having walking impediment applies not only to the muscles of lower limb but also to the back and abdominal muscles. Particularly, the weakening of the abdominal muscle can make it quite difficult to maintain the upright posture during walking. However, the prior art devices, such as those disclosed in Japanese Patent Application Laid-Open Publication No. 58-163364 (FIGS. 1-4) or Japanese Patent Application Laid-Open Publication No. 7-163607 (FIG. 1), are only capable of securely mounting the actuator near the joint, and are provided with virtually no function to assist the maintenance of the upright posture.

DISCLOSURE OF THE INVENTION

In view of such problems of the prior art, a primary object of the present invention is to provide a walking assistance device capable of favorably providing an assisting force for maintaining the upright posture while reducing the uncomfortable pressure upon the user.

According to the present invention, such an object can be accomplished by providing a walking assistance device comprising an assisting force generator (hip joint actuator 10) disposed at least on a side of a hip joint to provide an assisting force to a movement of a lower limb, where a hip support member (1) comprises: a back support (4) equipped with pads (18, 19, 20) for respectively abutting an intermediate portion between right and left erector spinae muscles, lateral outer sides of the spinae muscles and right and left iliac crests; and a belt (5) connected to the back support for tightening a lower part of an abdominal muscle.

Preferably, the pads (20) abutting the right and left iliac crests are provided on a detachable inner lining (6).

Particularly, the inner lining (6) preferably comprises a cushioning pad (21) interposed between the assisting force generator and a user's body.

The belt (5) may preferably comprise a pair of upper and lower belts (15U, 15L) attached to each of right and left ends of the back support, wherein the belts in each pair are integrally connected to corresponding right or left end of a buckle (16) disposed at a position corresponding to the lower part of the abdominal muscle.

Also, the belt (5) may comprise a pair of main belts (31) each having one end (31a) connected to associated one of right and left ends of the back support and the other end connected to associated one of right and left ends of a buckle disposed at a position corresponding to the lower part of the abdominal muscle, and a pair of sub belts (32) for connecting an upper part of the back support with a portion of each main belt corresponding to a side of the body.

According to the present invention as above, the following advantages can be obtained:

1. Because the hip support member for mounting the hip joint actuator as an assisting force generator for providing an assisting force to a movement of a lower limb comprises a back support equipped with pads for respectively abutting an intermediate portion between right and left erector spinae muscles, lateral outer sides of the spinae muscles and right and left iliac crests, and a belt connected to the back support for tightening a lower part of an abdominal muscle, it is possible to preferably support the lumbar vertebrae to steadily keep the upright posture without hampering bending movements of the waist. Further, the drive torque from the assisting force generator can be supported by the whole hip portion and this can eliminate the concern of inadvertent move of the support member during motion.
2. Because the pads abutting the right and left iliac crests are provided on a detachable inner lining, it is possible to cope with different builds of users by only changing the inner lining, and this can reduce the manufacturing cost.
3. Because a cushioning pad interposed between the assisting force generator and the user's body is provided to the inner lining, the body can be protected from an impact against the assisting force generator if the user happens to fall.
4. By attaching a pair of upper and lower belts (15U, 15L) to each of right and left ends of the back support, and connecting the belts in each pair integrally to corresponding right or left end of a buckle that is disposed at a position corresponding to the lower part of the abdominal muscle, it is possible to increase the abdominal cavity pressure to thereby lift up the viscera to proper positions.
5. Owing to the structure where the main belts connect the right and left ends of the back support to the right and left ends, respectively, of the buckle disposed at a position corresponding to the lower part of the abdominal muscle, and the sub belts connect an upper part of the back support to portions of the main belts corresponding to lateral sides of the body, it is possible to pull the upper part of the back support to make the back support closely contact the curve of the lumbar vertebrae, to whereby equalize the contact pressure of the hip support member along a circumference of the hip.

BEST MODE FOR CARRYING OUT THE INVENTION

Figure 1:
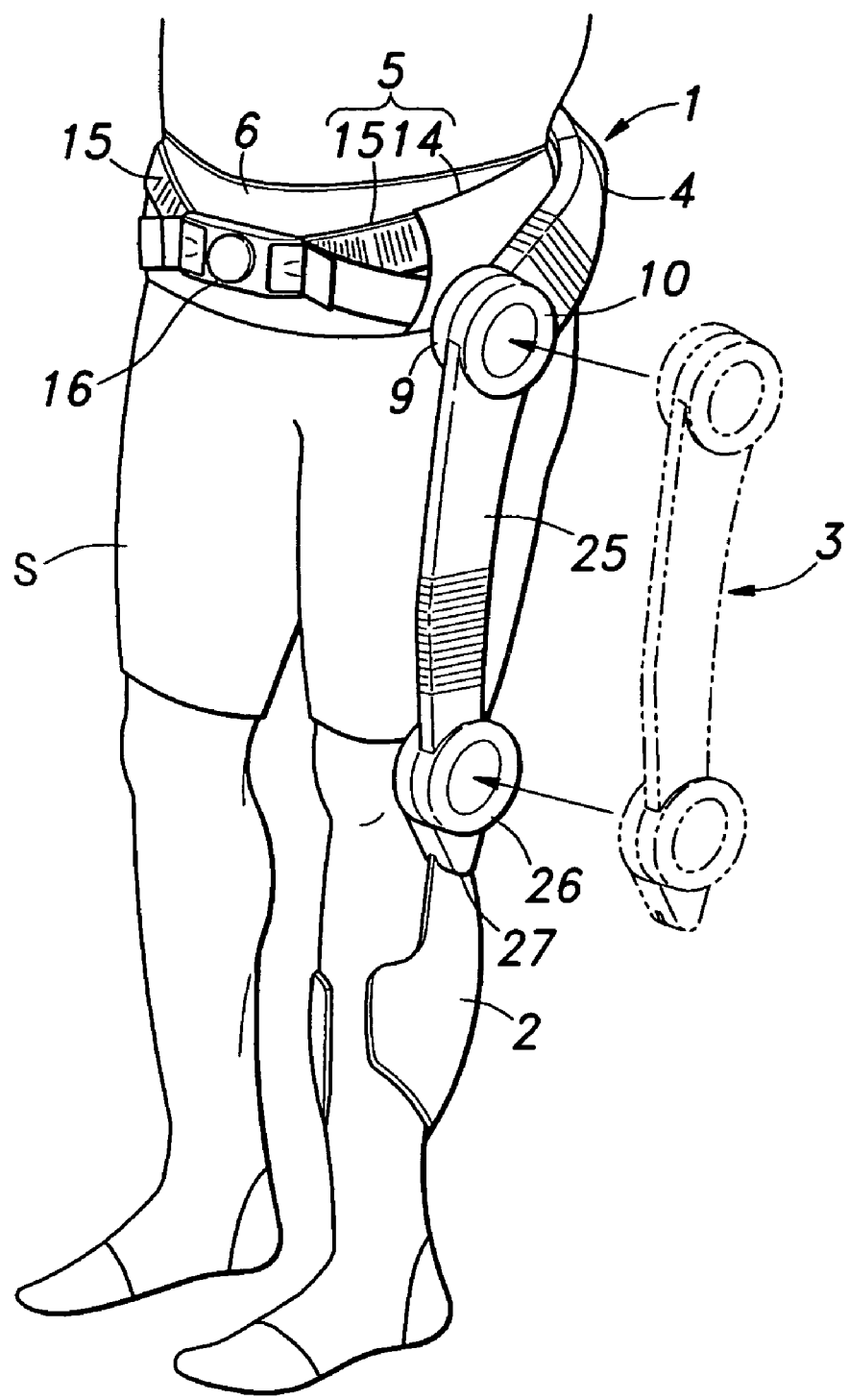
FIG. 1 is a perspective view showing a lower body on which a walking assistance device of the present invention is fitted.

FIG. 1 shows a walking assistance device of the present invention as worn on a user's body. The walking assistance device consists of a hip support member 1, lower leg support member 2 and a drive unit 3 for generating an assisting force, where the hip support member 1 and the lower leg support member 2 are secured on a lower limb and a rotational torque generated by the drive unit 3 is transmitted to the lower limb via the hip and lower leg support members, to whereby provide a force for supplementing a reduced muscle power.

Figure 2:
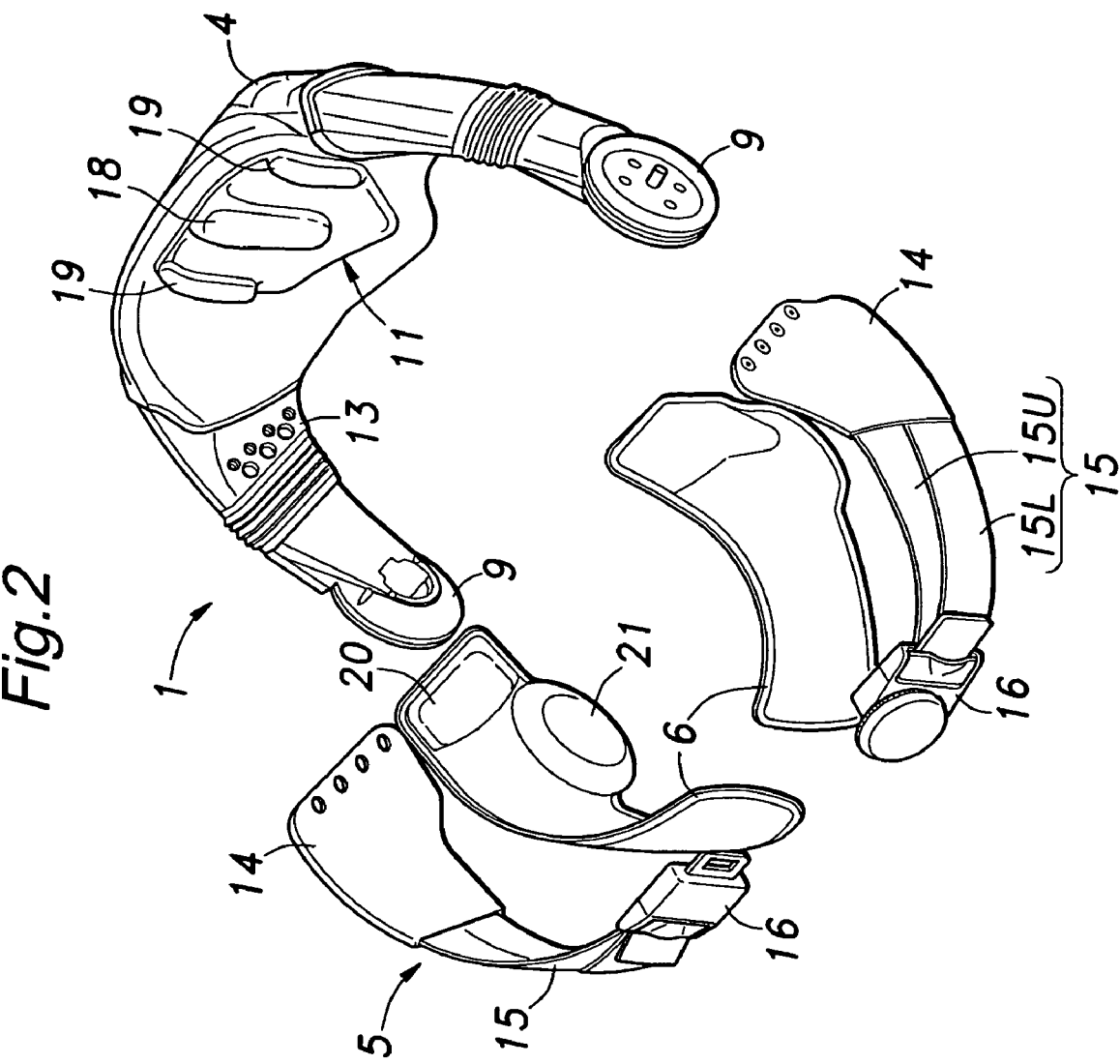
FIG. 2 is an exploded perspective view showing the structure of a hip support member of the walking assistance device according to the present invention.

The hip support member 1 comprises a back support 4, belt portion 5 and lining portion 6, as shown in FIG. 2.

Figure 3:
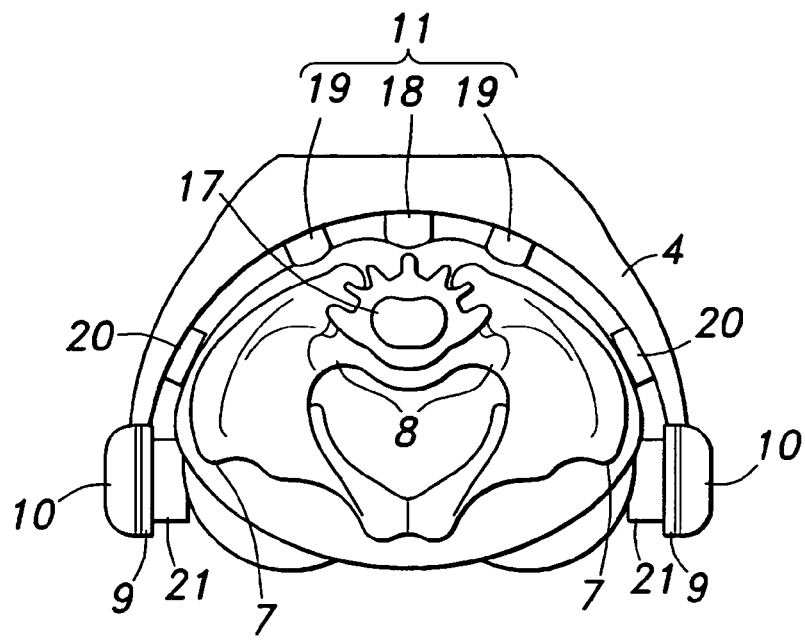
FIG. 3 is an explanatory drawing showing the relationship between a back support and the user's body.

Additionally referring to FIG. 3, the back support 4 is substantially of the shape of letter-U as seen in plan view so that it abuts a region of the body extending from right and left iliac crests (front ends of the pelvic bone) 7 to the backside of the sacroiliac joint point between the vertebrae and pelvic bone) 8, and consists of a substantially rigid body so as to withstand the drive force generated by a hip joint actuator 10, which consists of an electric motor equipped with a reduction gear or the like and is mounted on a hip drive source mount 9 provided at each of the right and left ends of the back support 4. A rear portion of the back support 4 has a hollow space so that a control circuit and a battery for supplying electric power to the control circuit as well as to the electric motor are accommodated therein, though not explicitly shown in the drawings. Further, at a portion of the back support 4 that directly abuts the user's body is provided a cushioning pad 11 of the present invention.

The belt portion 5 of the present invention comprises a pair of bases 14 made of a relatively rigid material such as a rubber material and attached by means of bolts to inner sides of belt joints 13 provided at right and left side portions of the back support 4, a pair of web parts 15 fixed to front ends of the bases 14, and a pair of right and left buckles 16 attached to front ends of the web parts 15. The inner surface of the belt portion 5, i.e., the surface facing the hip portion of the body, is adapted to be attached with the inner linings 6 for protection by means of loop and hook fastener or the like. The web parts 15 are woven so as to have an appropriate flexibility.

As shown in FIG. 3, the cushioning pad 11 provided to the back support 4 comprises a center pad 18 abutting a depression extending along a lumbar vertebra 17 and a pair of side pads 19 abutting laterally outer regions of erector spinae muscles slightly jutting out backward at right and left of the lumbar vertebra 17. Further, each inner lining 6 is provided with an iliac pad 20 abutting the iliac crest 7. Thus, a total of five pads abut principal portions of the hip to keep the back support 4 from moving out of place.

Further, because direct contact of the hip power transmitter 9 with the user's body would cause discomfort to the user and could impart a large impact on the body if the user happens to fall, hip joint pads 21 are provided to the inner linings 6 so as to be interposed between the user's body and the hip power transmitter 9 and reduce the impact and discomfort.

Each of the web parts 15 comprises a pair of upper and lower belts secured to the associated base 14, and the front ends of the belts are joined together and attached to the corresponding buckle 16 so that they form a shape of letter-V that converges in the front direction. The upper belt 15U of each web part 15 extends from the joint with the base 14 disposed at a position corresponding to the iliac crest 7 toward the buckle 16 disposed at an intermediate portion ("tanden") between the navel and pubic bone along a direction of the extension of muscle fibers of the abdominal external oblique muscle. The lower belt 15L of the web part 15 extends from the joint with the base 14 disposed on a side of the hip joint toward the buckle 16 along a direction of fibers of the abdominal internal oblique muscle.

The upright posture of the spine is maintained by the balance of back muscle, pectoral muscle and abdominal muscle. The weakening of muscles of a person having walking impediment applies not only to the muscles of lower limb but also to the back, pectoral or abdominal muscles. Particularly, the weakening of the abdominal muscle can lower the abdominal cavity and cause the spine to bend in the shape of letter-S as seen in side view, thus making it difficult to maintain the upright posture during walking. According to the present invention, the buckle 16 is positioned at a center of lower abdomen called "tanden" where the rectus abdominis muscle, abdominal external oblique muscle, abdominal internal oblique muscle, transversus abdominis muscle, etc. which play an important role in keeping the upright posture, overlap each other, and a tightening force is applied to the web parts 15 so that the back support 4 fitted on a region extending from the right and left iliac crests 7 to the backside of the secroiliac joint functions to correct the curve of the spine and stabilize the pelvis to achieve a proper posture and at the same time increase the abdominal cavity pressure to lift up the viscera to proper positions. Further, because the web parts 15 abut the lower abdominal portion with a relatively large contact area, the pressure applied to the abdominal cavity can be distributed evenly over the whole lower abdominal portion, thus reducing the uncomfortable pressure felt by the user.

Figure 4:
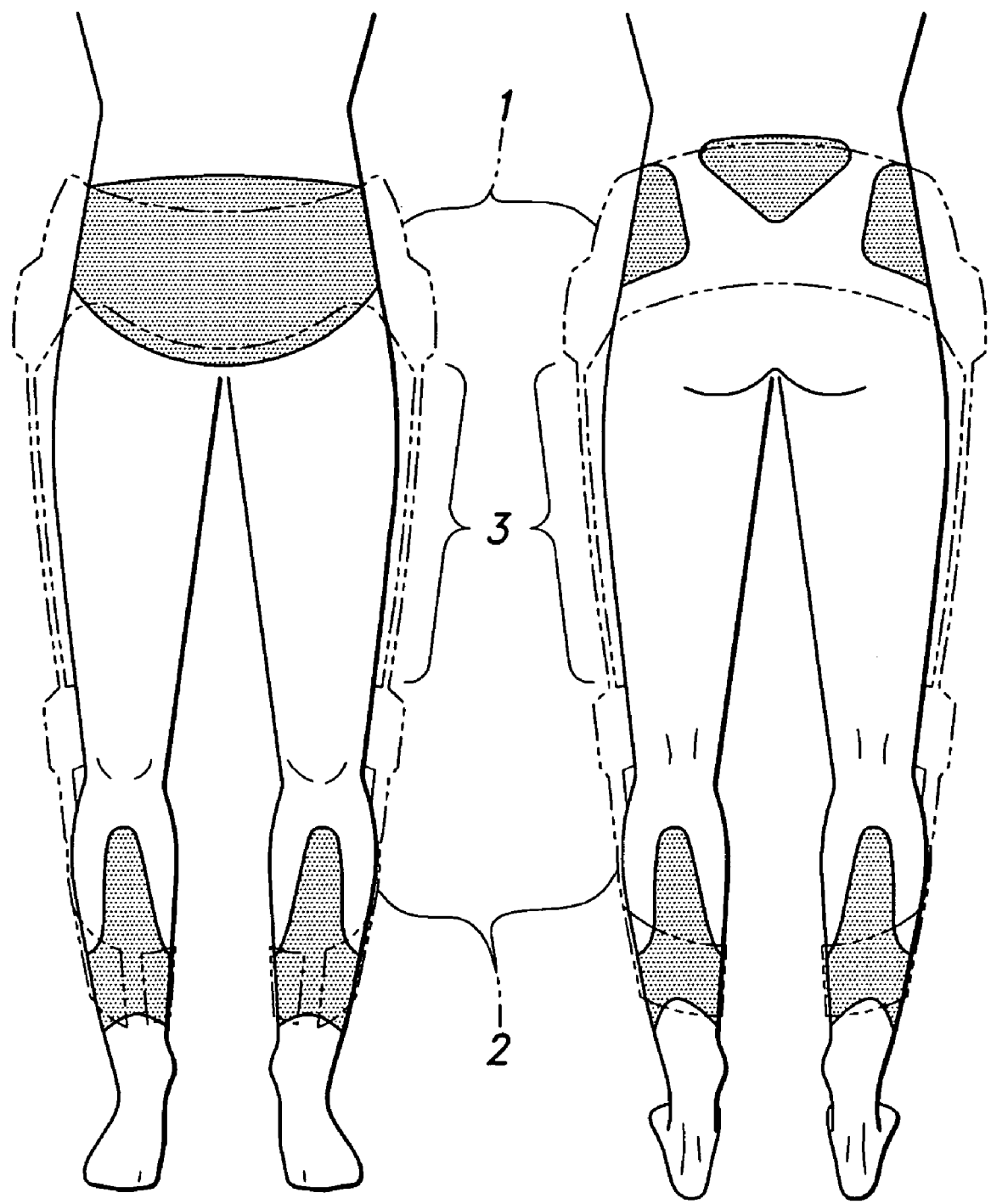
FIG. 4 is an explanatory drawing showing the relationship between the device of the present invention and the user's body.

As shown in FIG. 4, the back support 4 and belt portion 5 are adapted to engage the body portions (hatched regions of the hip in FIG. 4) where a relatively small amount of movement of skin occurs as the trunk or lower limb joint is moved. Owing to this feature, the motion of the hip joint relating to the lifting up and down of the thigh as well as the forward bending of the trunk will not be hampered, and the device will not be affected by the change in the circumferential length of the thigh due to expansion/contraction of the femoral muscles.

According to the above structure, the principal engagement points (five pads 18, 19, 20) of the back support 4 are provided on the backside, which has a relatively small difference in shape from person to person, and therefore, it is only necessary to change the belt portion 5 to cope with wearers of different builds and the back support 4 can be used in common, which contributes to a lower manufacturing cost of the hip support member 1.

Figure 5:
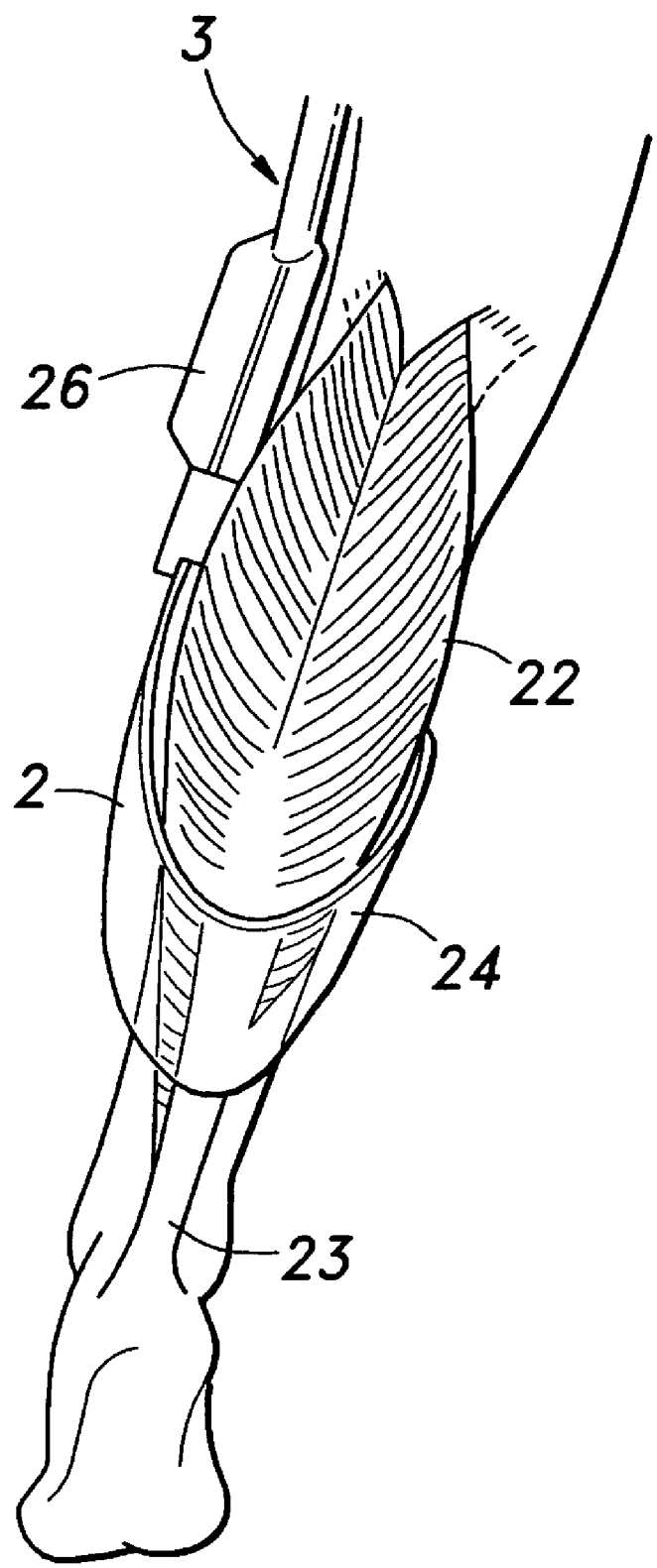
FIG. 5 is an explanatory drawing showing a lower leg support member fitted on a lower leg portion.

On the other hand, as also shown in FIG. 5, the lower leg support member 2 comprises a band-like member 24 wound around the lower leg portion so as to cover the region where the skin movement is relatively small (hatched regions of the lower leg in FIG. 4), i.e., region extending from lateral sides of an upper part of the anterior tibial muscle to the portion between a lower part of the calf muscle 22 and an upper part of the Achilles tendon 23. According to such a structure, it can be avoided to place the principal engagement points of the lower leg support member 2 on the calf, of which circumferential length can vary with the extension/flexion of the knee, or on the Achilles tendon where the skin moves with the motion of the ankle, and therefore it is possible to securely fasten the lower leg support member 2 on the lower leg with an abundant tightening force.

Figure 6:
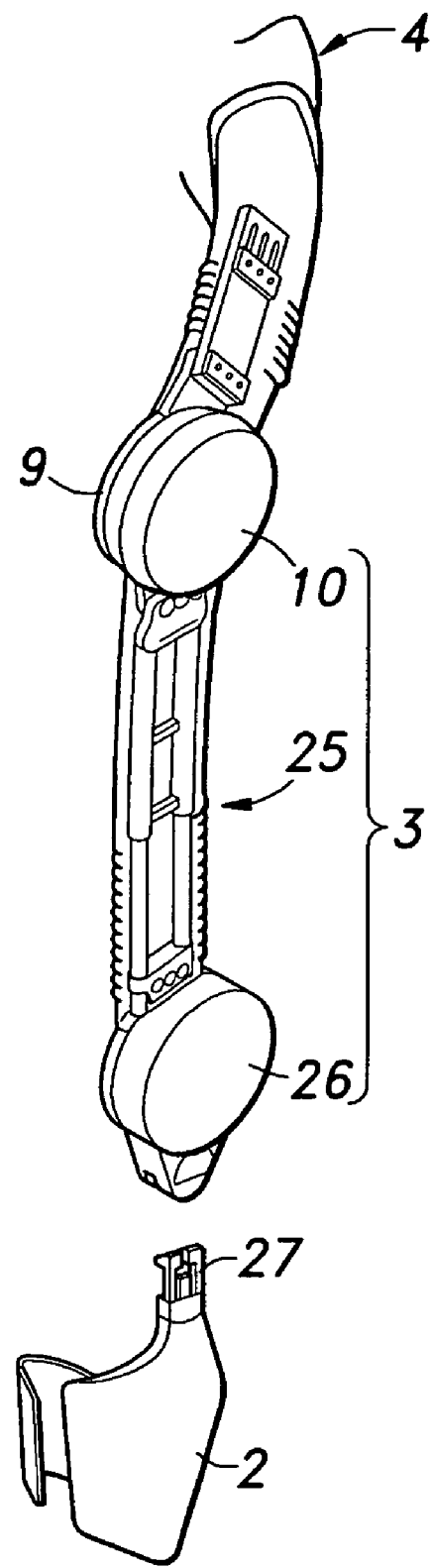
FIG. 6 is a perspective view of a drive unit.

Additionally referring to FIG. 6, the drive unit 3 comprises a hip joint actuator 10 and a knee joint actuator 26, each consisting of an electric motor equipped with a reduction gear or the like, where the actuators are attached to either end of a link bar 25 which is expandable and contractable in a telescopic fashion. The drive unit 3 is adapted so as to be detachable from the hip drive source mount 9 provided to the back support 4 at a position corresponding to a side of the hip joint as well as from a knee drive source mount 27 provided to the lower leg support member 2 at a position corresponding to a side of the knee joint. Because the hip support member 1, lower leg support member 2 and drive unit 3 are provided as separate members from one another, the user will not be required to take unnatural posture and can put on/off the device easily without help of other person.

Figure 7:
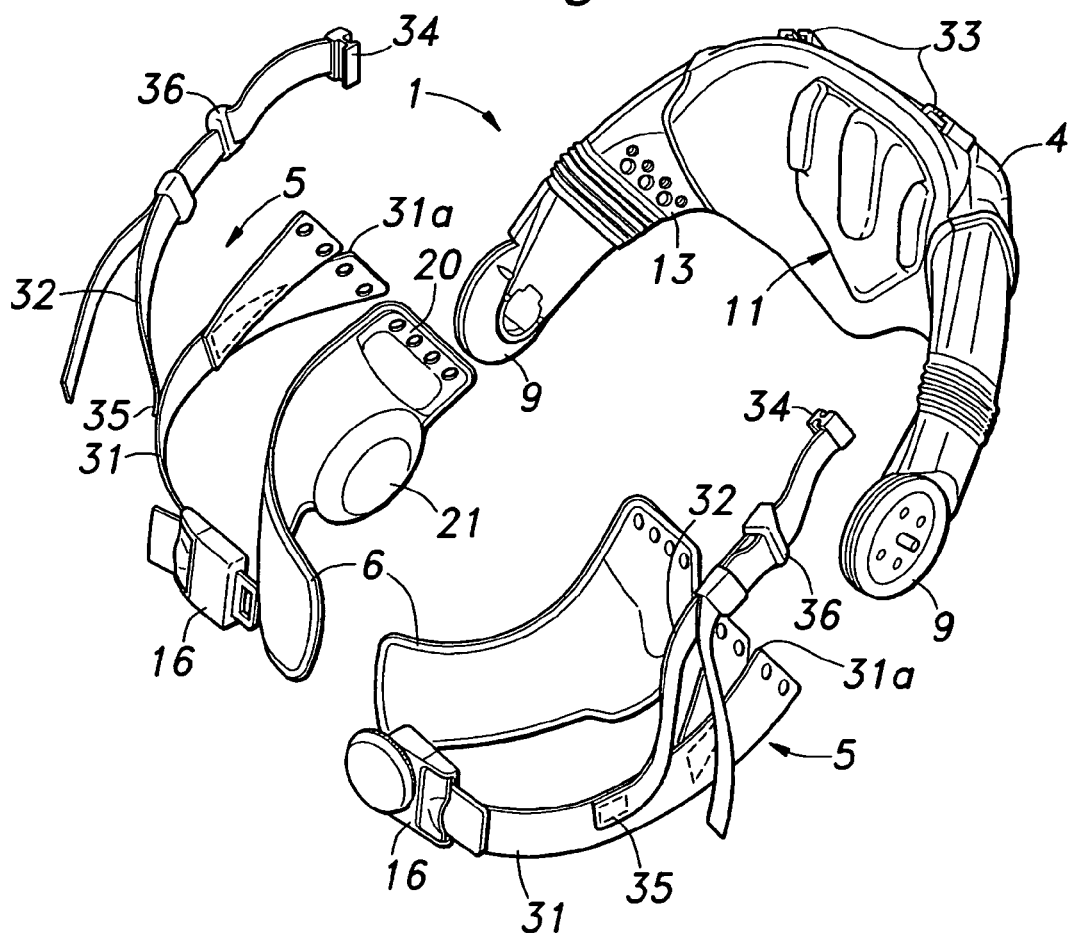
FIG. 7 is an exploded perspective view showing the structure of another embodiment of the belt portion (embodiment 2)

The shape of human body can vary widely depending on the differences in sex, age, etc. and in order to improve the fit of the hip support member 1 to the bodies of varying shapes without causing discomfort, it is preferred to arrange the hip support member 1 and the belt portion 5 so as to make the pressure of contact with portions of the body as even as possible. From such a point of view, FIG. 7 shows another embodiment of the belt portion 5 which is designed to further improve the fit of the walking assistance device.

The belt portion 5 of this embodiment comprises pair of right and left main belts 31 each having one end connected to associated one of the right and left belt joints 13 which are provided integrally to the back support 4 and the other end connected to the associated one of the right and left ends of the buckle 16, which is placed at a position corresponding to a lower part of the abdominal muscle, so that the length of the belts can be adjustable, and a pair of right and left sub belts 32 for connecting an upper part of the back support 4 to portions of the main belts 31 corresponding to the lateral sides of the body.

Each main belt 31 is made of a flexible material and the one end 31a thereof is widened to give the belt 31 a shape of letter-y to achieve firm attachment with the belt joint 13 having a large up-down dimension. Each sub belt 32 is given a thin shape to assume flexibility, and one end thereof is provided with an engagement member 34 that can be connected to and disconnected from one of laterally spaced engagement slots 33 provided to an upper end portion of the back support 4 while the other end thereof is sewn on the main belt 31. Further, at an intermediate portion between the two ends of the sub belt 32 is provided a buckle 36 for length adjustment.

Figure 8:
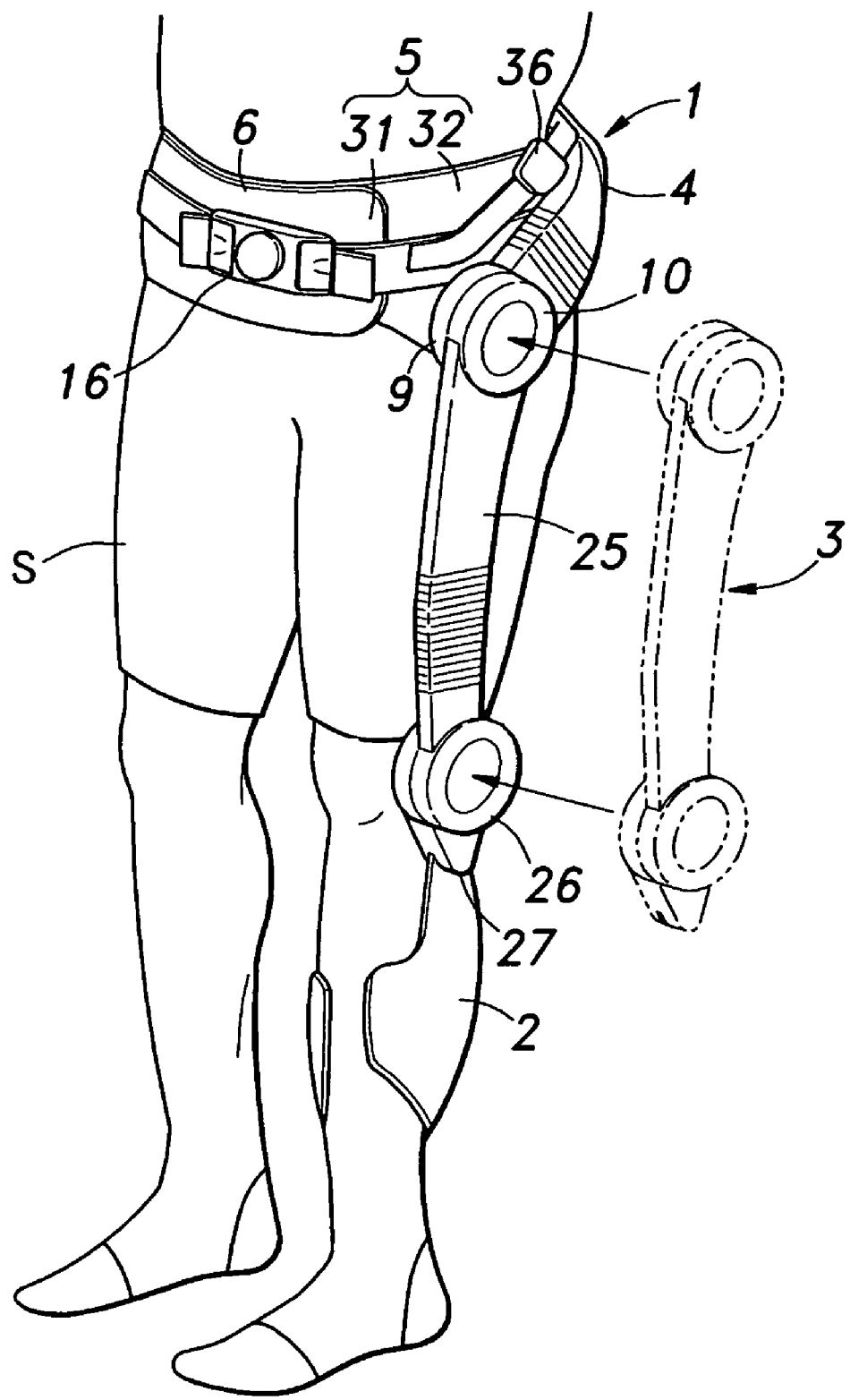
FIG. 8 is a perspective view showing a lower body fitted with the device shown in FIG. 7.

Now, with reference to FIG. 8, explanation is made to how the hip support member 1 of this embodiment can be worn by the user. First of all, the hip support member 1 is temporarily attached to the hip for rough positioning by using the inner linings 6 equipped with loop and hook fasteners.

Next, each main belt 31 is set to extend between the iliac crest 7 and the hip joint along the abdominal internal oblique muscle, and the buckles 16 are joined at the lower abdominal portion. Then, in this state, the lengths of the main belts 31 are adjusted such that the back support 4 is secured on the ilia of the backside of the body.

Subsequently, the lengths of the sub belts 32 are adjusted so as to make the back support 4 closely contact the curve of the lumbar vertebrae. Thus, owing to the pulling of the upper portion of the back support 4 by the sub belts 32, the state of contact between the back support 4 and the backside of the body can be stabilized and the contact pressure imposed by the whole hip support member 1 over the hip portion can be made more even, and further, the pressure variation caused by changes of the posture can be reduced.

If the device of the present invention is worn over a spat S for exercise that is adapted to provide a specific muscle(s) with a tightening force that is equivalent to that produced by taping (see Japanese Patent Application Laid-Open No. 2001-214303), the device can function even more effectively to improve the motion ability of the user in cooperation with the muscle support effect resulting from the tightening force produced by the fibers forming the spat S.

INDUSTRIAL APPLICABILITY

If the drive torque is effected in reverse, the walking assistance device of the present invention can apply a load torque upon the joint, and therefore the device can be used not only as a motion assisting device but also as a load generator for medical treatment, rehabilitation or training for muscle development.

The invention claimed is:

1. A walking assistance device comprising:
an assisting force generator disposed at least on a side of a hip joint, wherein the assisting force generator is configured to generate an assisting driving force to a movement of a lower limb; and
a hip support member for securely mounting the assisting force generator on a side of the hip joint,
wherein the hip support member comprises
a back support formed from a rigid material to substantially have a shape of letter-U as seen in plan view,
wherein the back support comprises a plurality of supporting individual pads, wherein a separate supporting pad is provided for an intermediate portion between right and left erector spinae muscles, for each lateral outer side of the spinae muscles, and for each of a right and a left iliac crest, and wherein the back support is configured to engage the hip principally at the individual pads; and
a belt connected to the back support for tightening a lower part of an abdominal muscle.

2. The walking assistance device according to claim 1, wherein the individual pads abutting the right and left iliac crests are provided on a detachable inner lining attached to the back support.

3. The walking assistance device according to claim 2, wherein the inner lining comprises a cushioning pad interposed between the assisting force generator and a user's body.

4. The walking assistance device according to claim 1, wherein the belt comprises a pair of upper and lower belts attached to each of right and left ends of the back support, wherein the belts in each pair are integrally connected to corresponding right or left end of a buckle disposed at a position corresponding to the lower part of the abdominal muscle.

5. The walking assistance device according to claim 1, wherein the belt comprises a pair of main belts each having one end connected to associated one of right and left ends of the back support and the other end connected to associated one of right and left ends of a buckle disposed at a position corresponding to the lower part of the abdominal muscle, and a pair of sub belts for connecting an upper part of the back support to a portion of each main belt corresponding to a side of the body.

* * * * *